(12) United States Patent
D'Ambrogio et al.

(10) Patent No.: US 9,949,907 B2
(45) Date of Patent: Apr. 24, 2018

(54) ORAL CARE COMPOSITIONS COMPRISING CALCIUM CARBONATE AND A CLAY

(71) Applicant: Colgate-Palmolive Company, New York, NY (US)

(72) Inventors: Robert D'Ambrogio, Princeton, NJ (US); Andrei Potanin, Hillsborough, NJ (US); Guisheng Pan, Philadelphia, PA (US); Nora Lin, Basking Ridge, NJ (US)

(73) Assignee: Colgate-Palmolive Company, New York, NY (US)

( * ) Notice: Subject to any disclaimer, the term of this patent is extended or adjusted under 35 U.S.C. 154(b) by 0 days.

(21) Appl. No.: 15/104,085

(22) PCT Filed: Dec. 16, 2013

(86) PCT No.: PCT/US2013/075310
§ 371 (c)(1),
(2) Date: Jun. 13, 2016

(87) PCT Pub. No.: WO2015/094154
PCT Pub. Date: Jun. 25, 2015

(65) Prior Publication Data
US 2017/0014321 A1    Jan. 19, 2017

(51) Int. Cl.
| | | |
|---|---|---|
| *A61Q 11/00* | (2006.01) | |
| *A61K 8/36* | (2006.01) | |
| *A61K 8/26* | (2006.01) | |
| *A61K 8/73* | (2006.01) | |
| *A61K 8/19* | (2006.01) | |
| *A61K 8/24* | (2006.01) | |
| *A61K 8/25* | (2006.01) | |
| *A61K 8/34* | (2006.01) | |

(52) U.S. Cl.
CPC ............. *A61K 8/36* (2013.01); *A61K 8/19* (2013.01); *A61K 8/24* (2013.01); *A61K 8/25* (2013.01); *A61K 8/26* (2013.01); *A61K 8/345* (2013.01); *A61K 8/73* (2013.01); *A61K 8/731* (2013.01); *A61Q 11/00* (2013.01); *A61K 2800/28* (2013.01); *A61K 2800/48* (2013.01); *A61K 2800/592* (2013.01)

(58) Field of Classification Search
CPC ..... A61Q 11/00; A61K 2800/48; A61K 8/731
See application file for complete search history.

(56) References Cited

U.S. PATENT DOCUMENTS

| | | | |
|---|---|---|---|
| 3,769,991 A | 6/1973 | McGrath | |
| 3,995,024 A | 11/1976 | Hawking et al. | |
| 4,325,939 A | 4/1982 | Shah | |
| 2003/0133882 A1* | 7/2003 | Kostinko | A61K 8/25 424/49 |
| 2004/0101494 A1* | 5/2004 | Scott | A61K 8/731 424/49 |
| 2005/0281758 A1* | 12/2005 | Dodd | A61Q 11/00 424/49 |
| 2011/0243861 A1* | 10/2011 | Vierling | A61K 8/044 424/58 |

FOREIGN PATENT DOCUMENTS

| | | | |
|---|---|---|---|
| WO | WO 1996/032090 | 10/1996 | |
| WO | WO 2004/087087 | 10/2004 | |
| WO | WO 2006/009679 | 1/2006 | |
| WO | WO 2007/063507 | 6/2007 | |
| WO | WO 2012057739 A1 * | 5/2012 | ............... A61K 8/19 |
| WO | WO 2013/007571 | 1/2013 | |

OTHER PUBLICATIONS

International Search Report and Written Opinion in International Application PCT/US2013/075310, dated Oct. 6, 2014.

* cited by examiner

*Primary Examiner* — Tracy Liu

(57) ABSTRACT

The present invention provides an oral care composition comprising, by total weight of the composition: (a) 15 to 35 weight % calcium carbonate; (b) 0.5 to 2 weight % cellulose ether thickening agent; (c) 1 to 6 weight % clay thickening agent; and (d) at least 35 weight % water; wherein, when the composition comprises less than 28 weight % calcium carbonate and less than 4 weight % clay thickening agent, the cellulose ether thickening agent is present in an amount of greater than 1 weight %.

18 Claims, No Drawings

ORAL CARE COMPOSITIONS COMPRISING CALCIUM CARBONATE AND A CLAY

BACKGROUND

Current calcium carbonate-based anti-cavity toothpastes typically utilize a high calcium carbonate loading with a water content of typically no greater than 30 to 40 weight %.

It would be desirable to provide more cost-effective calcium carbonate-based anti-cavity toothpastes, which exhibit consumer-acceptable characteristics such as acceptable viscosity and good chemical and physical stabilities.

BRIEF SUMMARY

The present invention provides an oral care composition comprising, by total weight of the composition: (a) 15 to 35 weight % calcium carbonate; (b) 0.5 to 2 weight % cellulose ether thickening agent; (c) 1 to 6 weight % clay thickening agent; and (d) at least 35 weight % water; wherein, when the composition comprises less than 28 weight % calcium carbonate and less than 4 weight % clay thickening agent, the cellulose ether thickening agent is present in an amount of greater than 1 weight %.

Optionally, the oral care composition comprises from 18 to 28 weight % calcium carbonate, based on the total weight of the composition. Further optionally, the oral care composition comprises from 20 to 27 weight % calcium carbonate, based on the total weight of the composition.

Optionally, the calcium carbonate comprises natural calcium carbonate.

Optionally, the calcium carbonate comprises precipitated calcium carbonate.

Optionally, the oral care composition comprises at least 40 weight % water, based on the total weight of the composition. Further optionally, the oral care composition comprises at least 50 weight % water, based on the total weight of the composition.

Optionally, the oral care composition comprises from 2.5 to 4 weight % clay thickening agent, based on the total weight of the composition.

Optionally, the clay thickening agent is a natural or synthetic clay comprising sodium, calcium, magnesium, lithium or potassium cations, or mixtures thereof. Optionally, the clay thickening agent is a smectite, bentonite, montmorillonite, hectorite or attipulgite clay. Further optionally, the clay thickening agent is magnesium aluminum silicate.

Optionally, the clay thickening agent is a synthetic layered silicate. Further optionally, the clay thickening agent is magnesium lithium silicate.

Optionally, the oral care composition comprises from 1 to 1.5 weight % cellulose ether thickening agent, based on the total weight of the composition.

Optionally, the cellulose ether thickening agent comprises carboxymethylcellulose, sodium carboxymethylcellulose, hydroxymethylcellulose, hydroxyethylcellulose or derivatives thereof, hydroxypropylcellulose or derivatives thereof, hydroxypropylmethylcellulose or derivatives thereof, or mixtures thereof.

Optionally, the cellulose ether thickening agent is sodium carboxymethyl cellulose.

Optionally, the composition further comprises microcrystalline cellulose.

Optionally, the microcrystalline cellulose is present in an amount of from 0.4 to 0.9 weight %, based on the total weight of the composition.

Optionally, the ratio of microcrystalline cellulose to cellulose ether thickening agent is from 1:1 to 1:3.5 by weight.

Optionally, the oral care composition comprises 20 to 27 weight % calcium carbonate, 1-1.5 weight % sodium carboxymethylcellulose and 2.5 to 4 weight % magnesium aluminum silicate, based on the total weight of the composition.

Optionally, the oral care composition comprises about 20 weight % calcium carbonate, about 1.4 weight % sodium carboxymethylcellulose and about 3.5 weight % magnesium aluminum silicate, based on the total weight of the composition Optionally, the oral care composition comprises about 27 weight % calcium carbonate, about 1.4 weight % sodium carboxymethylcellulose and about 3.5 weight % magnesium aluminum silicate, based on the total weight of the composition.

Optionally, the oral care composition further comprises an additional structuring agent.

Optionally, the additional structuring agent comprises a gum selected from xanthan gum, carrageenan, alginate gum, guar gum, gum arabic, locust bean gum, gum karaya, gellan gum, gum tragacanth, sclerotium gum, pullulan, konjac gum, rhamsan gum, welan gum, and derivatives thereof. Further optionally, the gum is selected from xanthan gum, carrageenan, alginate gum and guar gum. Further optionally, the gum is xanthan gum. Optionally, the oral care composition comprises the gum in an amount of from 0.05 to 1 weight %, based on the total weight of the composition.

Optionally, the additional structuring agent comprises a thickening silica. Further optionally, the oral care composition comprises the thickening silica in an amount of from 1 to 5 weight %, based on the total weight of the composition. Optionally, the oral care composition comprises the thickening silica in an amount of from 2 to 4 weight % and the clay thickening agent in an amount of from 1 to 2 weight %, based on the total weight of the composition.

Optionally, the ratio of thickening silica to clay thickening agent is from 4:1 to 2:1 by weight. Further optionally, the ratio of thickening silica to clay thickening agent is about 3:1 by weight.

Optionally, the oral care composition comprises the calcium carbonate in an amount of from 20 to 30 weight % and the cellulose ether thickening agent in an amount of from 1 to 2 weight %, based on the total weight of the composition.

Optionally, the oral care composition comprises the calcium carbonate in an amount of about 30 weight %, the clay thickening agent in an amount of about 1 weight %, the cellulose ether thickening agent in an amount of about 1.6 weight % and the thickening silica in an amount of about 3 weight %, based on the total weight of the composition.

Optionally, the oral care composition further comprises a preservative. Optionally, the preservative is selected from benzyl alcohol and parabens. Optionally, the preservative is present in an amount of from 0.1 to 1 weight %, based on the total weight of the composition.

Optionally, the oral care composition further comprises a humectant. Optionally, the humectant is selected from sorbitol, glycerin, xylitol, polyethylene glycol, propylene glycol, and combinations thereof.

Optionally, the humectant is sorbitol.

Optionally, the humectant is glycerin.

Optionally, the humectant is present in an amount of from 5 to 25 weight %, based on the total weight of the composition. Further optionally, the humectant is present in an amount of from 10 to 17 weight %, based on the total weight of the composition.

Optionally, the ratio of humectant to cellulose ether thickening agent is from 5:1 to 10:1 by weight. Further optionally, the ratio of humectant to cellulose ether thickening agent is from 8:1 to 8.5:1 by weight.

Optionally, the composition has a pH of from 9.2 to 10.2.

Optionally, the composition further comprises a buffer system, the buffer system being: (a) a combination of sodium silicate and tetrasodium pyrophosphate; (b) a combination of sodium hydroxide, sodium bicarbonate and tetrasodium pyrophosphate; or (c) a combination of sodium bicarbonate and sodium carbonate. Optionally, the buffer system is 0.25 to 0.75 weight % sodium silicate and 0.25 to 0.75 weight % tetrasodium pyrophosphate, based on the total weight of the composition. Optionally, the buffer system is 0.05 to 0.5 weight % sodium hydroxide, 0.25 to 0.75 weight % sodium bicarbonate and 0.25 to 1.5 weight % tetrasodium pyrophosphate, based on the total weight of the composition. Optionally, the buffer system is 0.05 to 0.5 weight % sodium bicarbonate and 0.2 to 0.6 weight % sodium carbonate, based on the total weight of the composition.

Optionally, the composition is a toothpaste, a tooth gel, or a combination thereof.

Optionally, the viscosity of the composition is from 100,000 to 1,000,000 cps as measured at 25° C. at 1 rpm using a Brookfield Viscometer Model HADV-II+Pro and a V74 spindle.

Optionally, the composition has a static yield stress of at least 50 Pa as measured at 25° C. using a Brookfield Viscometer Model HADV-II+Pro and a V74 spindle.

Further areas of applicability of the present invention will become apparent from the detailed description provided hereinafter. It should be understood that the detailed description and specific examples, while indicating the preferred embodiment of the invention, are intended for purposes of illustration only and are not intended to limit the scope of the invention.

DETAILED DESCRIPTION

The following description of the preferred embodiment(s) is merely exemplary in nature and is in no way intended to limit the invention, its application, or uses.

As used throughout, ranges are used as shorthand for describing each and every value that is within the range. Any value within the range can be selected as the terminus of the range. In addition, all references cited herein are hereby incorporated by referenced in their entireties. In the event of a conflict in a definition in the present disclosure and that of a cited reference, the present disclosure controls.

Unless otherwise specified, all percentages and amounts expressed herein and elsewhere in the specification should be understood to refer to percentages by weight. The amounts given are based on the active weight of the material.

The present inventors have found that the inclusion in high water content toothpaste compositions of particular concentrations of calcium carbonate, cellulose ether thickening agent and clay thickening agent results in compositions which have desirable viscosity and static yield stress. The compositions of the present invention were also found to be more cost-effective than previous "benchmark" formulations, and are chemically and physically stable. The compositions of the present invention also demonstrate reduced product stringiness, reduced product dry-out and enhanced stripe quality as compared to previous calcium carbonate-based formulations. The reduced thixotropic properties of the compositions of the invention as compared to previous "benchmark" compositions could also provide further benefits during the manufacturing process—for example, the compositions of the present invention are more easily and thoroughly transferred from mixing vessels and related piping during manufacture. This leads to a higher batch yield, and less residual product to be cleaned from the manufacturing equipment, thus the cleanout process requires less effort and reduced water consumption.

Accordingly, the present invention provides an oral care composition comprising, by total weight of the composition: (a) 15 to 35 weight % calcium carbonate; (b) 0.5 to 2 weight % cellulose ether thickening agent; (c) 1 to 6 weight % clay thickening agent; and (d) at least 35 weight % water; wherein, when the composition comprises less than 28 weight % calcium carbonate and less than 4 weight % clay thickening agent, the cellulose ether thickening agent is present in an amount of greater than 1 weight %.

In some embodiments, the oral care compositions comprise from 2 to 4.5 weight %; from 2.5 to 4 weight %; from 3 to 3.8 weight %; or about 3.5 weight % of the clay thickening agent, based on the total weight of the composition. In other embodiments, the oral care compositions comprise from 1 to 2 weight %; from 1 to 1.5 weight %; or about 1 weight % of the clay thickening agent, based on the total weight of the composition.

The clay thickening agent may be a natural or synthetic clay comprising sodium, calcium, magnesium, lithium or potassium cations, or mixtures thereof. In some embodiments, the clay thickening agent is a smectite, bentonite, montmorillonite, hectorite (such as Bentone® EW, LT from Rheox) or attipulgite (such as Attasorb® or Pharmasorb® from Enlgelhard, Inc.) clay, or mixtures thereof. Examples of smectite clays include beidellite, bentonite, hectorite, montmorillonite, saponite or stevensite. In some embodiments, the clay thickening agent is magnesium aluminum silicate (MAS). Magnesium aluminum silicate products are typically natural smectite (bentonite) clays that are water-washed to optimize purity and performance. One example of a magnesium aluminum silicate is Veegum® (R.T. Vanderbilt Holding Company, Inc.), which is a purified bentonite clay within the smectite class. Another example of a magnesium aluminum silicate is Science Brook® (Beijing Johnson Goldy Sci & Tech Co. Ltd.). Smectite clays are a class of natural mineral clays which exhibit high swelling/gelling and absorption properties, and can help to provide desirable structuring and rheology characteristics. A macroscopic smectite clay particle is composed of thousands of sandwiched platelets with a central alumina or magnesia layer joined to silica layers. The platelets have negatively charged platelet faces. Lattice discontinuities account for a very slight positive charge on the platelet edges. The net platelet charge is negative and the net negative charge on the platelet is mostly balanced by sodium ions. However, these charge-balancing ions associated with platelet faces are termed "exchangeable" since they can be readily substituted with other cations. When clay and water are mixed, water penetrates between platelets forcing them further apart and the cations begin to diffuse away from platelet faces. Once the platelets are separated the weakly positive platelet edges are attracted to the negatively charged platelet faces. A three dimensional colloidal structure forms, commonly called the "house of cards" which accounts for the characteristic rheology imparted by these clays. Magnesium aluminum silicate is used in certain embodiments of the high water content toothpaste formulas of the present invention as a key, cost effective structuring agent due to its ability to swell and bind water and also provide other benefits as described herein.

In some embodiments, the clay thickening agent is a synthetic layered silicate, for example magnesium lithium silicate (such as Laponite™ from Rockwood), however such clays may be less cost-effective.

In some embodiments, the oral care composition comprises the calcium carbonate in an amount of from 16 to 32 weight %; from 17 to 30 weight %; from 18 to 28 weight %; from 20 to 27 weight %; about 20 weight % or about 27 weight %, based on the total weight of the oral care composition. In other embodiments, the calcium carbonate is present in the composition in an amount of from 25 to 32 weight %; from 28 to 31 weight %; or about 30 weight %, based on the total weight of the composition. In some embodiments, the calcium carbonate is precipitated calcium carbonate (PCC), natural calcium carbonate (NCC), or a mixture thereof. In some embodiments, the calcium carbonate is precipitated calcium carbonate (PCC). In some embodiments, the calcium carbonate is natural calcium carbonate (NCC).

In some embodiments, the composition comprises at least 40 weight %; at least 45 weight %; at least 55 weight %, or at least 60 weight % water, based on the total weight of the composition. In some embodiments, the composition comprises from 35 to 70 weight %; from 40 to 65 weight %; or from 50 to 60 weight % water, based on the total weight of the oral care composition.

In some embodiments, the oral care composition comprises from 1 to 1.5 weight %; from 1.2 to 1.4 weight %; or about 1.4 weight % cellulose ether thickening agent, based on the total weight of the composition. In some embodiments, the cellulose ether thickening agent comprises carboxymethylcellulose (CMC), sodium carboxymethylcellulose (NaCMC), hydroxymethylcellulose (HMC), hydroxyethylcellulose (HEC) or derivatives thereof, hydroxypropylcellulose (HPC) or derivatives thereof, hydroxypropylmethylcellulose (HPMC) or derivatives thereof, or mixtures thereof. In some embodiments, the cellulose ether thickening agent is sodium carboxymethylcellulose. Typical commercial NaCMC options have a degree of substitution (DS) of from 0.7 to 1.2 (i.e. for every 10 anhydroglucose units, 7 to 12 hydroxy groups will be substituted with carboxymethyl groups). In general, CMC becomes more hydrophilic with increasing DS level, and the performance of the gum is modified with different DS. For the compositions of the present invention, NaCMC with degrees of substitution from 0.7 (Type 7) to 1.2 (Type 12) may be used. Particular examples of sodium carboxymethylcellulose which may be used in the present invention include NaCMC Type 7 (such as Gelycel® from Amtex Chemicals, LLC) and NaCMC Type 8 (such as CMC-TMS from Chongqing Lihong Fine Chemical Co. Ltd.).

In some embodiments, the compositions further comprise microcrystalline cellulose (MCC). An example of a source of MCC is Avicel® (FMC Corporation), which contains MCC in combination with NaCMC. Both Avicel® RC-591 (MCC containing 8.3 to 13.8 weight % NaCMC) and Avicel® CL-611 (MCC containing 11.3 to 18.8 weight % NaCMC) are suitable for use in the compositions of the present invention, although Avicel® CL-611 is preferred due to its greater ease of processing/dispersing. In certain embodiments, the microcrystalline cellulose is present in an amount of from 0.3 to 1 weight %; from 0.4 to 0.9 weight %; or 0.44 to 0.81 weight %, based on the total weight of the composition. In some embodiments, the ratio of microcrystalline cellulose to cellulose ether thickening agent is from 1:1 to 1:3.5; from 1:1.4 to 1:3.2; about 1:3 or about 1:1.6 by weight. In any of the above embodiments comprising microcrystalline cellulose, the cellulose ether thickening agent may be sodium carboxymethylcellulose. In certain such embodiments, the sodium carboxymethylcellulose may be present in an amount of from 1 to 1.5 weight %; from 1.2 to 1.4 weight %; or from 1.25 to 1.39 weight % based on the total weight of the composition.

In some embodiments, the oral care composition comprises 20 to 27 weight % calcium carbonate, 1-1.5 weight % sodium carboxymethylcellulose and 2.5 to 4 weight % magnesium aluminum silicate, based on the total weight of the composition. In some embodiments, the oral care composition comprises about 20 weight % calcium carbonate, about 1.4 weight % sodium carboxymethylcellulose and about 3.5 weight % magnesium aluminum silicate; or about 27 weight % calcium carbonate, about 1.4 weight % sodium carboxymethylcellulose and about 3.5 weight % magnesium aluminum silicate, based on the total weight of the composition.

In some embodiments, the oral care composition further comprises an additional structuring agent. In some embodiments, the additional structuring agent comprises a gum selected from xanthan gum, carrageenan, alginate gum, guar gum, gum arabic, locust bean gum, gum karaya, gellan gum, gum tragacanth, sclerotium gum, pullulan, konjac gum, rhamsan gum, welan gum, and derivatives thereof. In some embodiments, the gum is selected from xanthan gum, carrageenan, alginate gum and guar gum. In some embodiments, the gum is xanthan gum. Xanthan gum was found to provide structuring capabilities to the compositions without substantial viscosity build during manufacture of the compositions and during initial product aging (as discussed in the Examples, below). In some embodiments, the gum is present in the composition in an amount of from 0.05 to 1 weight %; 0.1 to 0.5 weight %; 0.15 to 0.3 weight %; or about 0.2 weight %, based on the total weight of the composition.

In some embodiments, the additional thickening agent comprises a thickening silica. In certain embodiments, the additional thickening agent is a thickening silica. In certain embodiments, the oral care composition includes the thickening silica in an amount of from 1 to 5 weight %; from 2 to 4 weight %; from 2.5 to 3.5 weight %; or about 3 weight %, based on the total weight of the composition. Examples of thickening silicas which may be used are Zeodent 165, Zeodent 163 and Zeodent 153 (from Huber); Aerosil® 200 and Sident® 22S (from Evonik); Sylodent® 15 and Perkasil® SM 660 (from W.R. Grace & Co.); Tixocil 43B (From Rhodia). In some embodiments, the oral care compositions comprise the thickening silica in an amount of from 2 to 4 weight % and the clay thickening agent in an amount of from 1 to 2 weight %; the thickening silica in an amount of from 2.5 to 3.5 weight % and the clay thickening agent in an amount of from 1 to 1.5 weight %; or the thickening silica in an amount of about 3 weight % and the clay thickening agent in an amount of about 1 weight % based on the total weight of the composition. In some embodiments, the ratio of thickening silica to clay thickening agent is from 4:1 to 2:1; from 3.5:1 to 2.5:1; about 3:1 by weight.

In any of the above embodiments comprising the thickening silica, the composition may comprise the calcium carbonate in an amount of from 20 to 30 weight % and the cellulose ether thickening agent in an amount of from 1 to 2 weight %; the calcium carbonate in an amount of from 25 to 30 weight % and the cellulose ether thickening agent in an amount of from 1.25 to 1.75 weight %; or the calcium carbonate in an amount of about 30 weight % and the cellulose ether thickening agent in an amount of about 1.6 weight %, based on the total weight of the composition. In certain embodiments, the oral care composition comprises the calcium carbonate in an amount of about 30 weight %, the clay thickening agent in an amount of about 1 weight %, the cellulose ether thickening agent in an amount of about 1.6 weight % and the thickening silica in an amount of about 3 weight %, based on the total weight of the composition.

In some embodiments, the compositions of the present invention also comprise an antibacterial or preservative agent, such as benzyl alcohol or parabens such as methylparaben and propylparaben. In some embodiments, the preservative is benzyl alcohol. The antibacterial or preservative agent may be present in the composition in an amount of from 0.1 to 1 weight %; 0.2 to 0.5 weight %; or about 0.3 weight % by total weight of the composition.

In some embodiments, the oral care compositions further comprise a humectant. In certain embodiments, the humectant is selected from sorbitol, glycerin, xylitol, polyethylene glycol, propylene glycol, and combinations thereof. In some embodiments, the humectant is glycerin. In some embodiments, the humectant is sorbitol. In certain embodiments, the humectant is present in the composition in an amount of from 5 to 25 weight %; from 7 to 23 weight %; from 9 to 17 weight %; or from 10 to 17 weight %, based on the total weight of the composition. In some embodiments, the ratio of humectant to cellulose ether structuring agent is from 5:1 to 10:1; from 8:1 to 8.5:1; or about 8.4:1 by weight. When the humectant is supplied as a solution in water, for example sorbitol as a 70 weight % solution in water, the amount of humectant is calculated as the active weight of the humectant, e.g. for a composition comprising 25 weight % sorbitol (as 70 weight % aqueous solution), the concentration of humectant is 17.5 weight %.

In some embodiments, the composition has a pH of from 8.5 to 10.5; or from 9.2 to 10.2. In certain embodiments, the composition comprises a buffer system, which may be: (a) a combination of sodium silicate and tetrasodium pyrophosphate; (b) a combination of sodium hydroxide, sodium bicarbonate and tetrasodium pyrophosphate; or (c) a combination of sodium bicarbonate and sodium carbonate. In some embodiments, the buffer system is 0.25 to 0.75 weight % sodium silicate and 0.25 to 0.75 weight % tetrasodium pyrophosphate; or about 0.4 weight % sodium silicate and 0.5 weight % tetrasodium pyrophosphate, based on the total weight of the composition. Various grades of sodium silicate are characterized by their $SiO_2:Na_2O$ ratio, which can vary between 1:2 and 1:3.75 by weight. Grades with this ratio being greater than 1:2.85 by weight are termed "alkaline". An example of a sodium silicate useful in the present invention is sodium silicate with target pH of 8.5, which has a $SiO_2:Na_2O$ ratio of 1:3.26 by weight and a relative density of 41 BE (BE denoting "Baume") and is denoted as "sodium silicate 1:3.26-41BE".

In some embodiments, the buffer system is 0.04 to 0.5 weight % sodium hydroxide, 0.25 to 0.75 weight % sodium bicarbonate and 0.25 to 1.5 weight % tetrasodium pyrophosphate; or about 0.04 weight % sodium hydroxide, about 0.5 weight % sodium bicarbonate and about 0.5 weight % tetrasodium pyrophosphate; or about 0.06 weight % sodium hydroxide, about 0.5 weight % sodium bicarbonate and about 0.5 weight % tetrasodium pyrophosphate based on the total weight of the composition. In some embodiments, the buffer system is 0.05 to 0.5 weight % sodium bicarbonate and 0.2 to 0.6 weight % sodium carbonate; or about 0.1 weight % sodium bicarbonate and 0.4 weight % sodium carbonate, based on the total weight of the composition.

In some embodiments, the oral care composition does not contain talc. In some embodiments, the oral care composition does not contain thickening silica. In some embodiments, the oral care composition does not contain talc or thickening silica.

In some embodiments, the oral care composition is a toothpaste, a tooth gel, or a combination thereof.

In some embodiments, the viscosity of the oral care composition is from 100,000 to 1,000,000; from 190,000 to 800,000 cps; from 200,000 to 800,000 cps; from 200,000 to 700,000 cps; from 300,000 to 600,000 cps; or from 300,000 to 500,000 cps, as measured at 25° C. at 1 rpm using a Brookfield Viscometer Model HADV-II+Pro and a V74 spindle. In some embodiments, the viscosity of the oral care composition immediately following its formation is from 100,000 to 1,000,000; from 190,000 to 800,000 cps; from 200,000 to 800,000 cps; from 200,000 to 700,000 cps; from 300,000 to 600,000 cps; or from 300,000 to 500,000 cps, as measured at 25° C. at 1 rpm using a Brookfield Viscometer Model HADV-II+Pro and a V74 spindle. In some embodiments, the viscosity of the oral care composition after storing for 1 day (24 hours) at 25° C./60% relative humidity (RH) in a sealed 5 fl. oz. laminate tube is from 100,000 to 1,000,000; from 190,000 to 800,000 cps; from 200,000 to 800,000 cps; from 200,000 to 700,000 cps; from 300,000 to 600,000 cps; or from 300,000 to 500,000 cps, as measured at 25° C. at 1 rpm using a Brookfield Viscometer Model HADV-II+Pro and a V74 spindle. In some embodiments, the viscosity of the oral care composition after storing for 3 days at 25° C./60% relative humidity in a sealed 5 fl. oz. laminate tube is from 100,000 to 1,000,000; from 190,000 to 800,000 cps; from 200,000 to 800,000 cps; from 200,000 to 700,000 cps; from 300,000 to 600,000 cps; or from 300,000 to 500,000 cps, as measured at 25° C. at 1 rpm using a Brookfield Viscometer Model HADV-II+Pro and a V74 spindle. In some embodiments, the viscosity of the oral care composition after storing for 1 week at 25° C./60% relative humidity in a sealed 5 fl. oz. laminate tube is from 100,000 to 1,000,000; from 190,000 to 800,000 cps; from 200,000 to 800,000 cps; from 200,000 to 700,000 cps; from 300,000 to 600,000 cps; or from 300,000 to 500,000 cps, as measured at 25° C. at 1 rpm using a Brookfield Viscometer Model HADV-II+Pro and a V74 spindle. In some embodiments, the viscosity of the oral care composition after storing for 1 month at 25° C./60% relative humidity in a sealed 5 fl. oz. laminate tube is from 100,000 to 1,000,000; from 190,000 to 800,000 cps; from 200,000 to 800,000 cps; from 200,000 to 700,000 cps; from 300,000 to 600,000 cps; or from 300,000 to 500,000 cps, as measured at 25° C. at 1 rpm using a Brookfield Viscometer Model HADV-II+Pro and a V74 spindle. In some embodiments, the viscosity of the oral care composition after storing for 2 months at 25° C./60% relative humidity in a sealed 5 fl. oz. laminate tube is from 100,000 to 1,000,000; from 190,000 to 800,000 cps; from 200,000 to 800,000 cps; from 200,000 to 700,000 cps; from 300,000 to 600,000 cps; or from 300,000 to 500,000 cps, as measured at 25° C. at 1 rpm using a Brookfield Viscometer Model HADV-II+Pro and a V74 spindle. In some embodiments, the viscosity of the oral care composition after storing for 3 months at 25° C./60% relative humidity in a sealed 5 fl. oz. laminate tube is from 100,000 to 1,000,000; from 190,000 to 800,000 cps; from 200,000 to 800,000 cps; from 200,000 to 700,000 cps; from 300,000 to 600,000 cps;

or from 300,000 to 500,000 cps, as measured at 25° C. at 1 rpm using a Brookfield Viscometer Model HADV-II+Pro and a V74 spindle.

In some embodiments, the composition has a static yield stress (YS) of at least 50 Pa; from 50 to 320 Pa; or from 80 to 290 Pa, as measured at 25° C. using a Brookfield Viscometer Model HADV-II+Pro and a V74 spindle. In some embodiments, the static yield stress of the composition immediately following its formation is at least 50 Pa; from 50 to 320 Pa; from 50 to 150 Pa; or from 80 to 140 Pa, as measured at 25° C. using a Brookfield Viscometer Model HADV-II+Pro and a V74 spindle. In some embodiments, the composition has a static yield stress of at least 50 Pa; from 50 to 320 Pa; from 50 to 170 Pa; from 50 to 150 Pa; or from 80 to 140 Pa as measured at 25° C. using a Brookfield Viscometer Model HADV-II+Pro and a V74 spindle after storing for 1 day (24 hours) at 25° C./60% relative humidity (RH) in a sealed 5 fl. oz. laminate tube In some embodiments, the composition has a static yield stress of at least 50 Pa; from 50 to 320 Pa; from 70 to 320 Pa; or from 100 to 260 Pa, as measured at 25° C. using a Brookfield Viscometer Model HADV-II+Pro and a V74 spindle after storing for 3 days at 25° C./60% relative humidity in a sealed 5 fl. oz. laminate tube. In some embodiments, the composition has a static yield stress of at least 50 Pa; from 80 to 320 Pa; or from 80 to 300 Pa, as measured at 25° C. using a Brookfield Viscometer Model HADV-II+Pro and a V74 spindle after storing for 1 week at 25° C./60% relative humidity in a sealed 5 fl. oz. laminate tube. In some embodiments, the composition has a static yield stress of at least 50 Pa; from 90 to 310 Pa; from 100 to 300 Pa; or about 290 Pa, as measured at 25° C. using a Brookfield Viscometer Model HADV-II+Pro and a V74 spindle after storing for 1 month at 25° C./60% relative humidity in a sealed 5 fl. oz. laminate tube. In some embodiments, the composition has a static yield stress of at least 50 Pa; from 100 to 300 Pa; from 110 to 290 Pa; or about 290 Pa, as measured at 25° C. using a Brookfield Viscometer Model HADV-II+Pro and a V74 spindle after storing for 2 months at 25° C./60% relative humidity in a sealed 5 fl. oz. laminate tube. In some embodiments, the composition has a static yield stress of at least 50 Pa; from 100 to 320 Pa; from 110 to 300 Pa; or about 290 Pa, as measured at 25° C. using a Brookfield Viscometer Model HADV-II+Pro and a V74 spindle after storing for 3 months at 25° C./60% relative humidity in a sealed 5 fl. oz. laminate tube.

The oral care compositions of the present invention may further comprise additional ingredients. These additional ingredients may include, but are not limited to, diluents, bicarbonate salts, surfactants, foam modulators, sweeteners, flavorants, pigments, antibacterial agents, anticaries agents, anticalculus or tartar control agents, and mixtures thereof.

In some embodiments, the oral care compositions of the present invention comprise at least one bicarbonate salt useful for example to impart a "clean feel" to teeth and gums due to effervescence and release of carbon dioxide. Any orally acceptable bicarbonate can be used, including without limitation, alkali metal bicarbonates such as sodium and potassium bicarbonates, ammonium bicarbonate and the like. The one or more additional bicarbonate salts are optionally present in a total amount of about 0.1 wt. % to about 50 wt. %, for example about 1 wt. % to 20 wt. %, by total weight of the composition.

The oral care compositions of the invention may also comprise at least one surfactant. Any orally acceptable surfactant, most of which are anionic, nonionic or amphoteric, can be used. Suitable anionic surfactants include without limitation, water-soluble salts of $C_{8-20}$ alkyl sulfates, sulfonated monoglycerides of $C_{8-20}$ fatty acids, sarcosinates, taurates and the like. Illustrative examples of these and other classes include sodium lauryl sulfate, sodium coconut monoglyceride sulfonate, sodium lauryl sarcosinate, sodium lauryl isethionate, sodium laureth carboxylate and sodium dodecyl benzenesulfonate. Suitable nonionic surfactants include without limitation, poloxamers, polyoxyethylene sorbitan esters, fatty alcohol ethoxylates, alkylphenol ethoxylates, tertiary amine oxides, tertiary phosphine oxides, dialkyl sulfoxides and the like. Suitable amphoteric surfactants include without limitation, derivatives of $C_{8-20}$ aliphatic secondary and tertiary amines having an anionic group such as carboxylate, sulfate, sulfonate, phosphate or phosphonate. Betaines may also be used, a suitable example of which is cocoamidopropyl betaine. One or more surfactants are optionally present in a total amount of about 0.01 wt. % to about 10 wt. %, for example, from about 0.05 wt. % to about 5 wt. %, or from about 0.1 wt. % to about 2 wt. % by total weight of the composition.

The oral care compositions of the invention may comprise at least one foam modulator, useful for example to increase amount, thickness or stability of foam generated by the composition upon agitation. Any orally acceptable foam modulator can be used, including without limitation, polyethylene glycols (PEGs), also known as polyoxyethylenes. High molecular weight PEGs are suitable, including those having an average molecular weight of 200,000 to 7,000,000, for example 500,000 to 5,000,000, or 1,000,000 to 2,500,000. One or more PEGs are optionally present in a total amount of about 0.1 wt. % to about 10 wt. %, for example from about 0.2 wt. % to about 5 wt. %, or from about 0.25 wt. % to about 2 wt. %, by total weight of the composition.

The oral care compositions of the present invention may comprise at least one sweetener (such as, for example, sodium saccharin), useful for example to enhance taste of the composition. One or more sweeteners are optionally present in a total amount depending strongly on the particular sweetener(s) selected, but typically 0.005 wt. % to 5 wt. %, by total weight of the composition, optionally 0.005 wt. % to 0.2 wt. %, further optionally 0.05 wt. % to 0.1 wt. % by total weight of the composition.

The compositions of the present invention may also comprise at least one flavorant, useful for example to enhance taste of the composition. Any orally acceptable natural or synthetic flavorant can be used, including without limitation tea flavours, vanillin, sage, marjoram, parsley oil, spearmint oil, cinnamon oil, oil of wintergreen (methylsalicylate), peppermint oil, clove oil, bay oil, anise oil, eucalyptus oil, citrus oils, fruit oils and essences including those derived from lemon, orange, lime, grapefruit, apricot, banana, grape, apple, strawberry, cherry, pineapple, etc., bean- and nut-derived flavors such as coffee, cocoa, cola, peanut, almond, etc., adsorbed and encapsulated flavorants and the like. Also encompassed within flavorants herein are ingredients that provide fragrance and/or other sensory effect in the mouth, including cooling or warming effects. Such ingredients illustratively include menthol, menthyl acetate, menthyl lactate, camphor, eucalyptus oil, eucalyptol, anethole, eugenol, cassia, oxanone, α-irisone, propenyl guaiethol, thymol, linalool, benzaldehyde, cinnamaldehyde, N-ethyl-p-menthan-3-carboxamine, N,2,3-trimethyl-2-isopropylbutanamide, 3-(1-menthoxy)-propane-1,2-diol, cinnamaldehyde glycerol acetal (CGA), menthone glycerol acetal (MGA) and the like. One or more flavorants are optionally present in a total amount of from about 0.01 wt.

% to about 5 wt. %, for example, from about 0.03 wt. % to about 2.5 wt. %, optionally about 0.05 wt. % to about 1.5 wt. %, further optionally about 0.1 wt. % to about 0.3 wt. % by total weight of the composition.

The compositions of the invention may comprise at least one colorant. Colorants herein include pigments, dyes, lakes and agents imparting a particular luster or reflectivity such as pearling agents. Any orally acceptable colorant can be used, including without limitation titanium dioxide, zinc oxide, red, yellow, brown and black iron oxides, ferric ammonium ferrocyanide, manganese violet, ultramarine, titaniated mica, bismuth oxychloride, and the like. One or more colorants are optionally present in a total amount of from about 0.001 wt. % to about 20 wt. %, for example, from about 0.01 wt. % to about 10 wt. %, or from about 0.1 wt. % to about 5 wt. %, by total weight of the composition.

The oral care compositions may also comprise a fluoride ion source. Fluoride ion sources include, but are not limited to: stannous fluoride, sodium fluoride, potassium fluoride, potassium monofluorophosphate, sodium monofluorophosphate (NaMFP), ammonium monofluorophosphate, sodium fluorosilicate, ammonium fluorosilicate, amine fluoride such as olaflur (N'-octadecyltrimethylendiamine-N,N,N'-tris(2-ethanol)-dihydrofluoride), ammonium fluoride, and combinations thereof. In certain embodiments the fluoride ion source includes stannous fluoride, sodium fluoride, amine fluorides, sodium monofluorophosphate, as well as mixtures thereof. In certain embodiments, the oral care composition of the invention may also contain a source of fluoride ions or fluorine-providing ingredient in amounts sufficient to supply about 50 to about 5000 ppm fluoride ion, e.g., from about 100 to about 1000, from about 200 to about 500, or about 250 ppm fluoride ion. Fluoride ion sources may be added to the compositions of the invention at a level of about 0.001 wt. % to about 10 wt. %, e.g., from about 0.003 wt. % to about 5 wt. %, 0.01 wt. % to about 1 wt., or about 0.05 wt. %. However, it is to be understood that the weights of fluoride salts to provide the appropriate level of fluoride ion will obviously vary based on the weight of the counter ion in the salt, and one of skill in the art may readily determine such amounts. A preferred fluoride salt may be sodium fluoride.

The compositions of the present invention may comprise a saliva stimulating agent useful, for example, in amelioration of dry mouth. Any orally acceptable saliva stimulating agent can be used, including without limitation food acids such as citric, lactic, malic, succinic, ascorbic, adipic, fumaric and tartaric acids, and mixtures thereof. One or more saliva stimulating agents are optionally present in saliva stimulating effective total amount.

The compositions of the present invention may include antisensitivity agents, e.g., potassium salts such as potassium nitrate, potassium bicarbonate, potassium chloride, potassium citrate, and potassium oxalate; capsaicin; eugenol; strontium salts; chloride salts and combinations thereof. Such agents may be added in effective amounts, e.g., from about 1 wt. % to about 20 wt. % by weight based on the total weight of the composition, depending on the agent chosen.

The composition of the invention may further comprise an antioxidant. Any orally acceptable antioxidant can be used, including butylated hydroxyanisole (BHA), butylated hydroxytoluene (BHT), vitamin A, carotenoids, vitamin E, flavonoids, polyphenols, ascorbic acid, herbal antioxidants, chlorophyll, melatonin, and mixtures thereof.

The compositions of the present invention may additionally optionally comprise a tartar control (anticalculus) agent as provided below. Tartar control agents among those useful herein include salts of the specified agents, including alkali metal and ammonium salts. The agents include: phosphates and polyphosphates, polyaminopropanesulfonic acid (AMPS), polyolefin sulfonates, polyolefin phosphates, diphosphonates such as azacycloalkane-2,2-diphosphonates (e.g., azacycloheptane-2,2-diphosphonic acid), N-methyl azacyclopentane-2,3-diphosphonic acid, ethane-1-hydroxy-1,1-diphosphonic acid (EHDP) and ethane-1-amino-1,1-diphosphonate, phosphonoalkane carboxylic acids and. Useful inorganic phosphate and polyphosphate salts include monobasic, dibasic and tribasic sodium phosphates, sodium tripolyphosphate, tetrapolyphosphate, sodium trimetaphosphate, sodium hexametaphosphate and mixtures thereof. Other useful tartar control agents include polycarboxylate polymers and polyvinyl methyl ether/maleic anhydride (PVM/MA) copolymers, such as GANTREZ®.

EXAMPLES

Example 1

The effect of varying the concentration of precipitated calcium carbonate (PCC), sodium carboxymethylcellulose (NaCMC) and magnesium aluminum silicate (MAS) in a dentifrice on the viscosity, static yield stress and overall physical stability thereof (as compared to a "benchmark" calcium carbonate-based toothpaste which contained 40 weight % PCC, 0.80 weight % NaCMC and no MAS) was studied.

The formulae tested are shown in Table 1, below:

TABLE 1

| Formula | A | B | C | D | E | Benchmark #1 |
| --- | --- | --- | --- | --- | --- | --- |
| Ppt. Calcium Carb.—PCC | 20.00 | 31.91 | 22.09 | 28.17 | 20.00 | 40.00 |
| Magnesium Aluminum Silicate | 5.32 | 2.00 | 6.00 | 3.96 | 3.83 | 0.00 |
| NaCMC Type 7/500T | 1.00 | 0.94 | 0.53 | 0.62 | 0.58 | 0.80 |
| Sorbitol, Non-Crystallizing (70 wt. % aq. soln.) | 23.00 | 23.00 | 23.00 | 23.00 | 23.00 | 20.00-30.00 |
| Tetrasodium Pyrophosphate | 0.50 | 0.50 | 0.50 | 0.50 | 0.50 | 0.25-0.75 |
| Sodium Silicate (1:3.26-41BE) | 0.40 | 0.40 | 0.40 | 0.40 | 0.40 | 0.25-0.75 |
| Demineralized Water | 45.44 | 36.89 | 44.12 | 39.01 | 47.33 | 25.00-35.00 |
| NaMFP | 1.10 | 1.10 | 1.10 | 1.10 | 1.10 | 1.00-1.50 |
| Sodium Lauryl Sulfate | 1.76 | 1.76 | 1.76 | 1.76 | 1.76 | 1.00-2.00 |
| Sodium Saccharin | 0.23 | 0.25 | 0.25 | 0.23 | 0.25 | 0.10-1.00 |
| Flavor | 0.95 | 0.95 | 0.95 | 0.95 | 0.95 | 0.95 |
| Benzyl Alcohol | 0.30 | 0.30 | 0.30 | 0.30 | 0.30 | 0.10-1.00 |

The viscosity of the above compositions was measured immediately after their formation ("initial"), and again after 1 week of storage and after 1 month of storage. The storage conditions were 25° C. and 60% relative humidity (RH), and the compositions were stored in sealed 5 fl. oz. laminate tubes with the tubes filled to capacity. The viscosity measurements were made using a Brookfield Viscometer model HADV-II+Pro and a V74 spindle, at 1 rpm and at 25° C.

The static yield stress (YS) of the above compositions was also measured immediately after their formation ("initial"), and again after 1 week of storage and after 1 month of storage at 25° C. and 60% relative humidity, with the compositions being stored in sealed 5 fl. oz. laminate tubes with the tubes filled to capacity. The static yield stress measurements were made using a Brookfield Viscometer model HADV-II+Pro and a V74 spindle, at 25° C.

The viscosity and static yield stress were measured on a Brookfield HADVII+Pro viscometer with spindle V-74 available from Brookfield Engineering Laboratories. All measurements on this viscometer were performed at room temperature (25° C.). In the tests, the spindle is rotated at a pre-set RPM (rotations per minute) series, while torque (Torque %) is reported in terms of % of its maximum (Tmax) as specified for the instrument (Tmax=1.437 mN·m for HADVII+Pro). Only those measurements with Torque % between 10 and 100% of Tmax are valid. The raw data (Torque % and RPM) were converted into shear stress (SS) and shear rate (SR) using well known formulas for Couette geometry, assuming that the vane (spindle) performs as its encompassing cylinder (i.e., assuming that paste between its blades move as a solid piece):

SR=SRC*RPM

SS=SF*Torque % where

SRC=$(\pi/15)C/(1-x^2)$

SF=$0.01*Tmax*C/(2\pi LR^2)$

C=$(1+x^2)/2$, where L is the vane blade length and R is the vane radius; and x is the ratio of spindle diameter to the diameter of the vessel in which the measurement is performed. (* denotes multiplication). Here L and R are in meters, Tmax is in N·m, SS is in Pascals and SR is in reciprocal seconds.

In the test, RPM was swept from 0.5 to 200 in 20 steps in logarithmical mode, 10 sec per step. "Viscosity" reported herein refers to SS/SR at 1 RPM (reported herein in centipoise, i.e. cps, wherein 1 cps=0.001 Pa·s). Furthermore, SS(SR) function was fitted with Casson equation, SS=$(Y^n+(V0*SR)^n)^{1/n}$ where Y, V0 and n are fitting parameters. Only the monotonously increasing section of the curve bended upward (i.e., the one in which both first and second derivative of SS(SR) were positive, typically above 1 RPM) was fitted. "Yield stress" reported herein refers to Y parameter.

The physical stability of each formula was also evaluated, i.e. the degree of separation of the mixture into two or more phases/layers after initial formation and after storage in sealed tubes for 3 months at three different temperature conditions (25° C./60% relative humidity; 40° C./75% relative humidity; and 49° C.). The physical stability of the formulas after 3 months aging at 40° C. and 75% relative humidity is reported in Table 2, below ("Separation Score"). This high-temperature aging is used as a predictive measure, and has been found to correlate well with two years' shelf-life determination under 25° C./60% relative humidity conditions. In these evaluations, a trained evaluator visually examines several attributes of the compositions under test, and provides a numeric rating of 0 to 4 (0=no separation; 1=slight separation; 2=minor; 3=moderate; 4=severe) for each attribute for each time point and for each set of storage conditions. The attributes are measured for: (1) a ribbon of the toothpaste squeezed from the tube (ribbon stand-up, cap separation, aeration, lumps/grit, graininess, discoloration); (2) tube cut open (appearance, aeration, separation, wall separation, clip separation, pocket, discoloration). The composition passes this visual inspection test if it achieved a rating of 3 or less in all of the indicated attributes. The average score specifically related to wall separation across at least three tubes for each formulation is reported in Table 2, below (as the "Separation Score"), with a score of three or less being acceptable ("pass") and a score of greater than three being unacceptable ("fail").

The viscosity measurements, yield stress measurements, and the separation score for each formulation are shown in Table 2, below.

TABLE 2

| Formula | A | B | C | D | E | Benchmark #1 |
|---|---|---|---|---|---|---|
| Viscosity (×10,000 cps)/YS (Pa) @ RT, V74 spindle | | | | | | |
| Initial | 23/95 | 21/142 | 27/129 | 38/95 | 25/42 | 24/110 |
| 1 week | 35/193 | 37/190 | 51/229 | 34/133 | 44/55 | 47/319 |
| 1 month | 34/193 | 42/215 | 62/290 | 49/255 | 48/63 | 56/353 |
| Separation Score | | | | | | |
| | 3.00 (Pass) | 2.51 (Pass) | 2.73 (Pass) | 2.62 (Pass) | 3.46 (Fail) | 2.48 (Pass) |

The characteristics of viscosity and static yield stress contribute towards product physical stability, bulk product transfer behavior during manufacturing, and also directly influence consumer-relevant properties of the composition such as ribbon standup (i.e. the ability of the toothpaste to hold its shape on the bristles after dispensing onto a toothbrush) and product squeezability from tubes. Compositions with yield stress ≥50 Pa and viscosity of 200,000 to 800,000 cps at all time points tested, and a Separation Score ≤3 are preferred.

It was observed in this example that less MAS was required in order to achieve the desired initial yield stress, viscosity and Separation Score when the compositions contained a higher concentration of calcium carbonate (approximately ≥28 weight %). However, it was also observed (across this example and the following examples) that, for compositions of low calcium carbonate concentration (i.e. less than 28 weight %), if the concentration of MAS was less than 4 weight %, then the composition did not have acceptable physical stability (with physical separation occurring within a short time), unless the concentration of NaCMC was greater than 1 weight %. For example, Formula E showed unacceptable levels of physical separation after less than 1 month aging at all temperature conditions.

Example 2

The effect upon the viscosity, static yield stress and Separation Score of varying the concentrations of NaCMC, MAS and humectant, while maintaining the concentration of PCC at a constant of 20 weight % was then studied. It has been shown in a parallel application by the present inventors that pellicle cleaning ratio (PCR) scores are comparable for formulations with 20 weight % calcium carbonate loading and those with 40 weight % calcium carbonate loading, thus cleaning performance would not be compromised by decreasing the calcium carbonate concentration. The formulas tested are shown in Table 3, below:

TABLE 3

| Formula | F | G | H | I | J | Benchmark #1 |
|---|---|---|---|---|---|---|
| Ppt. Calcium Carb.—PCC | 20.00 | 20.00 | 20.00 | 20.00 | 20.00 | 40.00 |
| Magnesium Aluminum Silicate | 5.38 | 3.15 | 4.44 | 5.73 | 7.03 | 0.00 |
| NaCMC Type 7/500T | 1.20 | 1.79 | 1.19 | 0.59 | 0.64 | 0.80 |
| Sorbitol, N.C. (70 wt. % aq soln) | 23.00 | 10.00 | 10.00 | 16.64 | 21.43 | 20.00-30.00 |
| Tetrasodium Pyrophosphate | 0.50 | 0.50 | 0.50 | 0.50 | 0.50 | 0.25-0.75 |
| Sodium Silicate (1:3.26-41BE) | 0.40 | 0.40 | 0.40 | 0.40 | 0.40 | 0.25-0.75 |
| Demineralized Water | 45.18 | 58.80 | 59.11 | 51.80 | 46.28 | 25.00-35.00 |
| NaMFP - USP | 1.10 | 1.10 | 1.10 | 1.10 | 1.10 | 1.00-1.50 |
| Sodium Lauryl Sulfate | 1.76 | 1.76 | 1.76 | 1.76 | 1.76 | 1.00-2.00 |
| Sodium Saccharin | 0.23 | 0.23 | 0.23 | 0.23 | 0.23 | 0.10-1.00 |
| Flavor | 0.95 | 0.95 | 0.95 | 0.95 | 0.95 | 0.95 |
| Benzyl Alcohol | 0.30 | 0.30 | 0.30 | 0.30 | 0.30 | 0.10-1.00 |

The viscosity, static yield stress and Separation Score of each of these formulas was measured, using the same methods/protocols as detailed in Example 1, above. The results are shown in Table 4.

The specific gravity of the formulas was also measured immediately after the formation of the compositions. A gravimetric method was utilized where a cylinder of known mass and volume was filled to capacity with the test product. The cylinder filled with test product was then weighed and the mass of the cylinder was then subtracted from the total mass to obtain the mass of the test product. The mass of the test product (in grams) was then divided by the volume of the cylinder (in milliliters) to obtain the specific gravity of the test product. The measurement was done at 25° C. and atmospheric pressure. The specific gravity of the formulations is reported in Table 4 as the specific gravity in relation to water, which has a specific gravity of 1 when measuring mass in grams and volume in milliliters (cubic centimeters) at 25° C. and atmospheric pressure.

TABLE 4

| Formula | F | G | H | I | J | Benchmark #1 |
|---|---|---|---|---|---|---|
| Viscosity (×10,000 cps)/YS (Pa) @ RT, V74 spindle | | | | | | |
| Initial | 37/54 | 20/50 | 25/83 | 30/113 | 35/88 | 24/110 |
| 1 week | 35/91 | 23/88 | 36/113 | 39/190 | 100/319 | 47/319 |
| 1 month | 80/193 | 29/93 | 40/113 | 51/233 | 130/390 | 56/353 |
| Separation Score | | | | | | |
| | 3.00 (Pass) | 2.89 (Pass) | 2.77 (Pass) | 2.41 (Pass) | 2.10 (Pass) | 2.48 (Pass) |
| Specific gravity | | | | | | |
| | 1.29 | 1.26 | 1.26 | 1.26 | 1.28 | 1.45 |

As seen above, formulas F to I all had the preferred characteristics of initial static yield stress (YS) ≥50 Pa, viscosity of 200,000 to 800,000 cps and Separation Score ≤3. However, it was found in this Example that higher MAS concentrations i.e. greater than about 6 weight %, were not acceptable due to very high viscosity build during extended aging (see, for example, the 1 week and 1 month viscosity measurements obtained for Formula J in Table 4, above). Despite being physically and chemically stable, such high-MAS formulas would be difficult to dispense from tubes and difficult to disperse during brushing, and are hence less desirable to consumers.

The above formulae F to I were also found to have reduced specific gravity as compared to the benchmark composition (containing 40 weight % PCC), and could thus deliver further cost savings in geographical regions where filling of toothpaste tubes/dispensers is controlled by the volume of the tube/dispenser (rather than the weight of the composition). It is believed that the compositions of Table 3, above, would be more cost-effective than the benchmark composition (and also the compositions of Table 1), as well as having desirable viscosity, yield stress and physical stability scores.

Example 3

The MAS/NaCMC concentrations were optimized in these experiments for improved stability and further cost savings. In formulations K to N (shown in Table 5), the concentration of the humectant (sorbitol) was adjusted so as to keep a constant ratio of 8.4:1 by weight sorbitol: NaCMC (in terms of active humectant—the sorbitol used in these compositions was a 70 weight % solution in water, hence the 8.4:1 by weight sorbitol:NaCMC ratio equates to a ratio of 12:1 by weight "sorbitol (70 weight % aq. soln.)" to NaCMC).

The viscosity, static yield stress and Separation Score of each of these formulas was measured, using the same methods/protocols as detailed in Example 1, above. The concentration of soluble fluoride ion (in ppm) present in the compositions, and the pH of a 10 weight % solution of the compositions in deionized water, were measured immediately after the formation of the compositions, and again after one, two and three months aging at controlled room temperature (25° C. and 60% relative humidity) and accelerated high temperature conditions (40° C. and 75% relative humidity) in sealed 5 fl. oz. laminate tubes with the tubes filled to capacity. The results for the initial measurement and the measurements at three months are reported in Table 5, below. The specific gravity of the compositions was also determined, using the method as described above. The results are shown in Table 5, below:

TABLE 5

| | Formula | | | | |
|---|---|---|---|---|---|
| | K | L | M | N | Benchmark #1 |
| Ppt. Calcium Carb. - PCC | 20.00 | 20.00 | 20.00 | 20.00 | 40.00 |
| Magnesium Aluminum Silicate | 3.50 | 4.00 | 2.86 | 3.85 | 0.00 |
| NaCMC Type 7/500T | 1.40 | 1.18 | 1.14 | 1.25 | 0.80 |
| Sorbitol, N.C. (70 wt. % aq soln) | 16.80 | 14.12 | 13.71 | 15.02 | 20.00-30.00 |
| Tetrasodium Pyrophosphate | 0.50 | 0.50 | 0.50 | 0.50 | 0.25-0.75 |
| Sodium Silicate (1:3.26-41BE) | 0.40 | 0.40 | 0.40 | 0.40 | 0.25-0.75 |
| Demineralized Water | 53.04 | 55.44 | 57.03 | 54.62 | 25.00-35.00 |
| NaMFP - USP | 1.10 | 1.10 | 1.10 | 1.10 | 1.00-1.50 |
| Sodium Lauryl Sulfate | 1.76 | 1.76 | 1.76 | 1.76 | 1.00-2.00 |
| Sodium Saccharin | 0.23 | 0.23 | 0.23 | 0.23 | 0.10-1.00 |
| Flavor | 0.95 | 0.95 | 0.95 | 0.95 | 0.95 |
| Benzyl Alcohol | 0.30 | 0.30 | 0.30 | 0.30 | 0.10-1.00 |
| Viscosity (×10,000 cps)/YS (Pa) @ RT, V74 spindle | | | | | |
| Initial | 32/86 | 47/129 | 19/63 | 45/113 | 24/110 |
| 1 Month | 33/290 | 50/129 | 29/110 | 46/142 | 56/353 |
| 2 Month | 42/290 | 51/129 | 37/110 | 51/170 | 58/353 |
| 3 Month | 50/290 | 62/193 | 37/110 | 54/129 | 61/353 |
| pH (10% Solution) | | | | | |
| Initial | 9.74 | 9.78 | 9.50 | 9.67 | 9.61 |
| 3 months@25° C./60% RH | 9.74 | 9.72 | 9.48 | 9.64 | 9.61 |
| 3 months@40° C./75% RH | 9.62 | 9.68 | 9.45 | 9.60 | 9.60 |
| Soluble $F^+$, ppm | | | | | |
| Initial | 1440 | 1455 | 1510 | 1451 | 1455 |
| 3 months@25° C./60% RH | 1350 | 1038 | 1384 | 1288 | 1038 |
| 3 months@40° C./75% RH | 1070 | 970 | 1010 | 1017 | 913 |
| Specific Gravity | | | | | |
| | 1.26 | 1.24 | 1.23 | 1.24 | 1.45 |
| Separation Score | | | | | |
| | 2.60 (Pass) | 2.87 (Pass) | 2.95 (Pass) | 2.74 (Pass) | 2.48 (Pass) |

The results obtained, above, indicated that the most preferred formulae are those containing 2.5 to 4 weight % magnesium aluminum silicate and 1 to 1.5 weight % sodium carboxymethylcellulose. Among these preferred formulae, Formula K (with 3.5 weight % MAS and 1.4 weight % NaCMC) was the most preferred due to it having a rheology profile which was the closest match to that of the Benchmark formula (formula S), and superior physical stability (lower Separation Score) as compared to the remaining test formulations. Formula K also provides significant cost savings as compared to Benchmark formula S.

Compositions K to N also exhibit reduced specific gravity as compared to the "benchmark" formulation. The reduced specific gravity can provide additional formula cost savings in geographical regions where product containers are filled and marketed by volume rather than by weight. The reduced fill weight requires less raw material/product manufacturing to meet inventory demands. However, the product provides the same theoretical brushings per tube since consumers measure by visual dispensing (ribbon length approximately covers toothbrush bristles) rather than by weight.

Example 4

Formulas containing either sorbitol or glycerin as the humectant, and either natural calcium carbonate (NCC) or precipitated calcium carbonate (PCC) as the abrasive were also developed. The pH of these formulas was targeted to between 9.2 and 10.2 in order to ensure chemical stability of the fluoride active (sodium monofluorophosphate, NaMFP) and to maximize microbial robustness. Different buffering systems were utilized to maintain this pH range. The following buffer systems were found to be effective: 1) sodium silicate and tetrasodium pyrophosphate; or 2) sodium hydroxide, sodium bicarbonate and tetrasodium pyrophosphate; or 3) sodium carbonate and sodium bicarbonate. Also, 0.3 weight % benzyl alcohol was found to effectively enhance robustness to microbial insult in these high water formulations.

Lower concentrations of magnesium aluminum silicate (MAS) can be utilized with high concentrations of abrasive without resulting in excessive viscosity build in the compositions during aging/shelf life (as discussed in Example 1). Thickening silica may optionally be added to such formulas to provide further water binding and higher initial viscosity in order to more closely match the viscosity profile of the benchmark formulations. Formula R in Table 5 is an example of a composition.

Three month aging evaluations (at controlled room temperature i.e. 25° C./60% relative humidity, and accelerated high temperature conditions i.e. 40° C./75% relative humidity) confirm acceptable chemical and physical stability of the formulations. The viscosity, static yield stress, Separation Score, specific gravity, pH and soluble fluoride concentration were evaluated as detailed in Examples 1 to 3. The results are shown in Table 6, below:

TABLE 6

| | \multicolumn{5}{c}{Formula} | | | | |
|---|---|---|---|---|---|
| | O | P | Q | R | S (benchmark) |
| Ppt. Calcium Carb. - PCC | 20.00 | 27.00 | 0.00 | 0.00 | 0.00 |
| Natural Calcium Carbonate - NCC | 0.00 | 0.00 | 20.00 | 30.00 | 42.00 |
| Magnesium Aluminum Silicate | 3.50 | 3.50 | 3.50 | 1.00 | 1.00 |
| NaCMC Type 7/500T | 1.40 | 1.40 | 0.00 | 0.00 | 0.00 |
| NaCMC Type 8 | 0.00 | 0.00 | 1.80 | 1.60 | 1.00 |
| Sorbitol, N.C. (70 wt. % aq soln) | 0.00 | 0.00 | 21.00 | 21.00 | 15.00-25.00 |
| Glycerin - Vegetable Derived | 13.00 | 10.00 | 0.00 | 0.00 | 0.00 |
| Thickener Silica | 0.00 | 0.00 | 0.00 | 3.00 | 2.00 |
| Tetrasodium Pyrophosphate | 0.50 | 0.50 | 0.00 | 0.00 | 0.00 |
| Sodium Bicarbonate | 0.50 | 0.50 | 0.10 | 0.10 | 0.05-1.00 |
| Sodium Carbonate (Soda Ash) | 0.00 | 0.00 | 0.40 | 0.40 | 0.20-0.60 |
| Sodium Hydroxide (38 wt. % aq Sol'n) | 0.10 | 0.10 | 0.00 | 0.00 | 0.00 |
| Demineralized Water | 56.76 | 52.76 | 48.95 | 38.65 | 25.00-35.00 |
| NaMFP - USP | 1.10 | 1.10 | 1.10 | 1.10 | 1.00-1.50 |
| Sodium Lauryl Sulfate | 1.76 | 1.76 | 1.90 | 1.90 | 1.00-2.00 |
| Sodium Saccharin | 0.23 | 0.23 | 0.15 | 0.15 | 0.10-1.00 |
| Flavor | 0.85 | 0.85 | 0.80 | 0.80 | 1.00 |
| Benzyl Alcohol | 0.30 | 0.30 | 0.30 | 0.30 | 0.10-1.00 |
| Viscosity (×10,000 cps)/YS (Pa) @ RT, V74 spindle | | | | | |
| Initial | 24/85 | 32/133 | 26/129 | 59/319 | 51/290 |
| 1 Month | 34/129 | 44/290 | 32/193 | 64/290 | 55/319 |
| 2 Month | 39/233 | 51/290 | 35/193 | 66/290 | 57/319 |
| 3 Month | 45/233 | 57/290 | 38/193 | 67/319 | 59/319 |
| pH (10% Solution) | | | | | |
| Initial | 9.55 | 9.66 | 9.88 | 9.90 | 10.00 |
| 3 months@25° C./60% RH | 9.53 | 9.65 | 9.86 | 9.71 | 9.80 |
| 3 months@40° C./75% RH | 9.49 | 9.62 | 9.83 | 9.55 | 9.58 |
| Soluble F$^+$, ppm | | | | | |
| Initial | 1462 | 1412 | 1463 | 1460 | 1480 |
| 3 months@25° C./60% RH | 1120 | 1212 | 1102 | 1430 | 1430 |
| 3 months@40° C./75% RH | 942 | 957 | 980 | 1220 | 1350 |
| Specific Gravity | | | | | |
| | 1.24 | 1.27 | 1.31 | 1.39 | 1.52 |
| Separation Score | | | | | |
| | 2.88 (Pass) | 2.89 (Pass) | 2.80 (Pass) | 2.21 (Pass) | 2.16 (Pass) |

The above compositions O to P were all found to have the desired viscosity, static yield stress, Separation Scores, and chemical stability (pH and soluble fluoride concentration on aging), as well as having specific gravity below that of the benchmark composition, Formula S. The advantages of reduced specific gravity are discussed in Example 5, above.

Example 7

Xanthan gum and microcrystalline cellulose (MCC) were also evaluated as additional structuring agents in combination with MAS and NaCMC in the high water calcium carbonate toothpaste compositions in order to determine potential synergistic benefits.

Xanthan gum was investigated in a lead formulation with 3.5 weight % MAS and 1.4 weight % NaCMC (Formula P from Table 6, above), in order to improve the processing and tube filling characteristics of this formula. The gel phase of Formula P required a high torque mixer for its preparation due to high viscosity and yield stress properties. Improved processing was achieved by adding xanthan gum and decreasing NaCMC proportionally in this formula (see Formula T of Table 7). Xanthan gum was found to provide structuring capabilities without substantial viscosity build during batch making and initial product aging.

It is believed that microcrystalline cellulose (MCC) may enhance particulate mouthfeel and flavor release attributes in high water content compositions. Avicel® CL-611 (MCC containing 11.3 to 18.8 weight % NaCMC) was evaluated in Formulae W and X, below, as compared to Formulae U and V, respectively.

TABLE 7

| Formula | T | U | V | W | X | Y (Benchmark) |
|---|---|---|---|---|---|---|
| Ppt. Calcium Carbonate—PCC | 27.00 | 27.00 | 27.00 | 27.00 | 27.00 | 41.00 |
| Avicel CL-611 | 0.00 | 0.00 | 0.00 | 0.50 | 1.00 | 0.00 |
| Magnesium Aluminum Silicate | 3.50 | 3.50 | 3.50 | 3.50 | 3.50 | 0.00 |
| NaCMC Type 7/500T | 1.20 | 1.30 | 1.40 | 1.20 | 1.20 | 1.00 |
| Xanthan gum | 0.20 | 0.20 | 0.20 | 0.20 | 0.20 | 0.00 |

TABLE 7-continued

| Formula | T | U | V | W | X | Y (Benchmark) |
|---|---|---|---|---|---|---|
| Glycerin, vegetable - USP | 9.00 | 9.00 | 9.00 | 9.00 | 9.00 | 12.00-18.00 |
| Tetrasodium Pyrophosphate | 0.50 | 0.50 | 0.50 | 0.50 | 0.50 | 0.25-0.75 |
| Sodium Bicarbonate | 0.50 | 0.50 | 0.50 | 0.50 | 0.50 | 0.25-0.75 |
| Sodium Hydroxide (50 wt. % aq Sol'n) | 0.08 | 0.08 | 0.08 | 0.08 | 0.08 | 0.05-0.50 |
| NaMFP - USP | 1.10 | 1.10 | 1.10 | 1.10 | 1.10 | 1.00-1.50 |
| Sodium Lauryl Sulfate | 1.76 | 1.76 | 1.76 | 1.76 | 1.76 | 1.00-2.00 |
| Sodium Saccharin | 0.25 | 0.25 | 0.25 | 0.25 | 0.25 | 0.10-1.00 |
| Flavor | 0.85 | 0.85 | 0.85 | 0.85 | 0.85 | 0.95 |
| Benzyl Alcohol | 0.30 | 0.30 | 0.30 | 0.30 | 0.30 | 0.10-1.00 |
| Demineralized Water | 53.76 | 53.66 | 53.56 | 53.26 | 52.76 | 30.00-40.00 |
| Viscosity (×10,000 cps)/YS (Pa) @ RT, V74 spindle | | | | | | |
| Initial | 23/86 | 25/52 | 32/85 | 30/129 | 38/129 | 22/118 |
| 1 day | 28/94 | 33/83 | 40/85 | 29/129 | 38/170 | 32/257 |
| 3 days | 30/129 | 36/120 | 40/110 | 32/190 | 43/255 | 40/290 |
| 1 Week | 36/235 | 30/210 | 40/210 | 30/235 | 40/290 | 45/290 |
| 1 Month | 38/235 | 34/210 | 41/210 | 36/255 | 41/310 | 48/290 |
| Separation Score | | | | | | |
| | 2.82 (Pass) | 2.80 (Pass) | 2.89 (Pass) | 2.62 (Pass) | 2.65 (Pass) | 2.68 (Pass) |
| Foaming Attributes (SITA Foam Test) | | | | | | |
| Foam Volume (ml) | 179 | 170 | 177 | 190 | 194 | 175 |
| Foam Stability/Decay (ml) | 207 | 190 | 200 | 214 | 216 | 195 |

A flavor study was conducted on the formulas containing 0 weight %, 0.5 weight % and 1.0 weight % Avicel® (formulas T, W and X, respectively). The formulas were evaluated "fresh" (1 week aged at room temperature) and after 6 weeks aging at both CRT and 49° C. to compare flavor release and general mouthfeel attributes. No significant benefits related to flavor release were found in these calcium carbonate-based formulas containing Avicel®. However, it was observed that the inclusion of Avicel® in the compositions could provide improved foam volume during brushing.

The foam properties of Formulas T to X (and the benchmark, Y) were quantified by means of an in-vitro lab test called a SITA foam tester (model R-2000, manufactured by SITA Messtechnik GmbH). The instrument provides automated agitation of diluted toothpaste preparations to mimic mechanical action experienced during brushing and has been found to correlate well with sensory ratings by expert (trained) panelists. The SITA foam tester quantifies foam generation and decay utilizing an array of needles that monitor changes in electroconductance. Changes in foam volume are reported by the instrument at predetermined time intervals up to 1 minute after a pre-determined amount of agitation has been applied to the test solution (for example, the foam volume is measured every 5 seconds, with the agitation being temporarily stopped while the measurement takes place). Similarly, foam decay is measured at predetermined time intervals up to one minute but with no further agitation of the solution (i.e. the foam decay measurement starts after the 1 minute of agitation). The results in Table 7 are reported for peak foam volume during foam generation and foam volume after one minute of decay. Without wishing to be bound by any theory, it is believed that foam volume is lower for these examples during the SITA agitation process than during foam decay due to the agitation partially breaking down the foam, which then re-builds somewhat in a delayed fashion after agitation is stopped (possibly due to the settling of ingredients which may disrupt the foam structure).

250 milliliters of a solution of 4:1 water:toothpaste (by weight) was used for all SITA tests, and a stir blade rotating at 800 rpm provided agitation. The foam volume was measured at time t=0 and then at 5 second intervals up to 60 seconds total time (with the agitation being temporarily stopped while the measurements took place). The data in Table 7 indicates that there is an increase in foam generation and stability with increasing concentration of Avicel®.

The inclusion of Avicel® in the formulations also appears to provide enhanced viscosity, enhanced static yield stress and reduced stringiness in the formulations. In comparing Formulas W and X with Formulas U and V, respectively, and comparing these four formulas with Formula T, it can be seen that viscosity and yield stress of the compositions comprising Avicel® are superior to equivalent formulas which contain no MCC, but which have an even greater concentration of NaCMC type 7 than that provided by the addition of 0.5 or 1 weight % Avicel® CL-611 to a 1.2 weight % NaCMC-containing composition (for example, comparing Formula W with Formula U; and Formula X with Formula V). It is noted that Avicel® does not provide adequate structuring when substituted for MAS (as shown in Table 7a, below). Rather, it provides supplemental structuring combined with MAS in these high water calcium carbonate formulations. Reduced stringiness benefits are discussed in Example 8, below.

TABLE 7a

| | Formula # | |
|---|---|---|
| | T | No MAS |
| Ppt. Calcium Carbonate - PCC | 27.00 | 27.00 |
| Avicel CL-611 | 0.00 | 3.50 |
| Thickener Silica | 0.00 | 0.00 |
| Magnesium Aluminum Silicate | 3.50 | 0.00 |
| NaCMC Type 7/500T | 1.20 | 1.20 |
| Xanthan gum | 0.20 | 0.20 |
| Glycerin, vegetable - USP | 9.00 | 9.00 |
| Tetrasodium Pyrophosphate | 0.50 | 0.50 |
| Sodium Bicarbonate | 0.50 | 0.50 |

TABLE 7a-continued

|  | Formula # | |
|---|---|---|
|  | T | No MAS |
| Sodium Hydroxide (50 wt. % aq Sol'n) | 0.08 | 0.08 |
| NaMFP - USP | 1.10 | 1.10 |
| Sodium Lauryl Sulfate | 1.76 | 1.76 |
| Sodium Saccharin | 0.25 | 0.25 |
| Flavor | 0.85 | 0.85 |
| Benzyl Alcohol | 0.30 | 0.30 |
| Demineralized Water | 53.76 | 53.76 |
| Viscosity (×10,000 cps)/YS (Pa) @ RT, V74 spindle | | |
| Initial | 23/86 | 12/28 |
| 1 day | 28/94 | 15/28 |
| 3 days | 30/129 | 16/39 |
| 1 Week | 36/235 | 21/31 |
| 1 Month | 38/235 | 26/43 |
| Separation Score | | |
|  | 2.82 (Pass) | 4.18 (Fail) |

Example 8

Certain rheology characteristics of toothpastes are important for consumer acceptance. For example, it is generally desirable that a dentifrice does not separate with aging, is easy to dispense from a toothpaste tube, demonstrates good ribbon properties without strings, and distributes evenly and smoothly over the teeth. It is also desirable that the product does not dry out readily when exposed to air (as discussed in Example 9, below). High water MAS/PCC and MAS/NCC formulations were developed to meet these criteria and in some cases improve on the performance of benchmark formulas (for example, in displaying significantly reduced stringiness compared to the benchmark formula). Reduced stringiness also indicates less product retention in equipment during manufacturing, thus resulting in more efficient processing and easier cleaning/sanitizing of equipment. It also indicates cleaner product dispensing from the tube and less messy cap/orifice buildup over time.

As a means to quantify stringiness, a toothpaste sample was loaded into a cup held in a fixed position and a probe was lowered into the sample. More specifically, the cup was 7 mm deep and 24 mm wide, the probe was a Nylon ball, 16 mm in diameter, and the initial gap between the ball and the bottom of the cup was 4 mm. After 1 min rest, the probe is raised out of the toothpaste sample at a steady rate. The point at which the toothpaste ribbon (stretched between the sample in the cup and the probe) breaks is then recorded. Table 8 shows resulting stringiness values of optimized formulas of Tables 6 and 7. The data is an average of three measurements at both 10 mm/sec and 30 mm/sec separation speeds. As can be seen, formulas P, T, W and X display significantly reduced stringiness compared to the benchmark

TABLE 8

| Toothpaste stringiness measurements | | | | | |
|---|---|---|---|---|---|
| | Formulas | | | | |
| | P | T | W | X | Y (Benchmark) |
| Breakup Time (Sec) @ 10 mm/sec | 1.80 | 1.93 | 1.87 | 1.62 | 2.24 |

TABLE 8-continued

| Toothpaste stringiness measurements | | | | | |
|---|---|---|---|---|---|
| | Formulas | | | | |
| | P | T | W | X | Y (Benchmark) |
| Breakup Time (Sec) @ 30 mm/sec | 0.68 | 0.75 | 0.70 | 0.58 | 1.24 |

Example 9

Calcium carbonate formulations in general have an inherent propensity to dry out if consumers are not vigilant in closing the cap of the toothpaste tube after usage. Product that has dried can become more difficult to dispense due to increased viscosity and may result in other sources of consumer dissatisfaction due to loss of flavor and increased mess due to cracked/crumbling product. However, the present inventors have discovered that compositions of the present invention tend to dry out less rapidly. The total calcium carbonate loading is also a contributing factor and, as discussed above, the compositions of the present invention (which utilize a clay thickening agent and cellulose ether thickening agent) enable formulas with significantly reduced calcium carbonate to be prepared.

A rheology test was developed to quantify toothpaste dry-out when exposed to air. In this test, increase in dry-out is expressed by an increase in relative elastic modulus over time as measured by a surface probe. More specifically, the surface probe is a de Nouy ring (RI 01 by Kruss) and it is mounted on a TA ARG2 rheometer with an attachment (supplied by TA Instruments) for surface rheology. In this evaluation, a test sample was deposited on the rheometer Peltier plate at 30° C. using a plastic bounding ring and leveled with a spatula so as to form a layer 71 mm in diameter and 6 mm in height. Then the de Nouy ring was descended on the sample so as to be positioned exactly on the surface. Oscillatory torque of 10 µN·m was applied at 1 Hz frequency and surface elastic modulus, G', was recorded as a function of time for 10 minutes. The relative increase of G' (defined as the value of G' after 10 minutes compared to its initial value) for Formula P and for the benchmark formula Y were recorded. A lower value of Relative Increase of G' indicates less product dry-out. In these tests, Formula P of Table 6 exhibits significantly reduced product dry-out compared to the benchmark toothpaste "Y" (which contains 40 weight % PCC).

TABLE 9

| Toothpaste dry-out measurements | |
|---|---|
| Formula | Relative increase of G' |
| Benchmark Y (of appendix 5) | 4.3 |
| Formula "P" (of appendix 4) | 2.1 |

Example 10

A thixotropic fluid is a fluid which takes a finite time to attain equilibrium viscosity when introduced to a step change in shear rate. A fluid (e.g. a toothpaste) showing more rapid recovery towards a steady (equilibrium) viscosity value following a step change in shear rate (as described below) displays reduced thixotropy. It has been found that toothpastes of reduced thixotropy provide improved stripe quality. Also, it has been found that MAS provides reduced thixotropy and thus enhanced stripe quality in calcium carbonate toothpaste. Low concentrations of MAS up to about 1%, as demonstrated by formula "S", above, have been utilized in otherwise stable formulas of high calcium carbonate loading for the purpose of providing enhanced stripe quality.

The toothpaste formulations of the present invention may be used to produce both white paste and multi-striped products.

Rheology evaluations were conducted to compare thixotropy/predictive stripe quality of the toothpaste formulations of the present invention against toothpastes without MAS. These experiments determine recovery time of samples in terms of relative shear stress as it evolves after a switch from $100 \text{ sec}^{-1}$ to $1 \text{ sec}^{-1}$ of applied shear. The point at which the relative stress reaches a certain fraction of its equilibrium value (e.g., 80% or 90%, i.e. "T80" and "T90") may be taken to quantify the recovery time of the respective products.

defined as the "equilibrium stress" corresponding to a shear rate of $1 \text{ sec}^{-1}$. Recovery time T80 is defined as the time (t) at which the shear stress first reaches 80% of the equilibrium stress after passing through the undershoot. Time t is measured starting from t=0 (as defined above). Similarly, recovery time T90 is defined as the time (t) at which the shear stress reaches 90% of the equilibrium stress after passing through the undershoot (time t being measured starting from t=0, as defined above).

A shorter/faster recovery time is believed to indicate better stripe quality potential. The results in Table 10 show that the high water MAS formulations of the present invention have the fastest recovery time and would provide the best stripe quality compared to non-MAS counterparts. In fact, recovery time measured for compositions of the present invention is comparable to the benchmark "S" standard, which is currently utilized for stripe aesthetics). Thus, the compositions of the present invention exhibit reduced thixotropy compared to calcium carbonate formulas without MAS and impart rheology properties to the finished formula that ensure excellent stripe quality.

TABLE 10

| Formula | R | S (Benchmrk) | T | Y (Benchmrk) | Z | ZZ |
|---|---|---|---|---|---|---|
| Ppt. Calcium Carbonate | 0.00 | 0.00 | 27.00 | 41.00 | 0.00 | 0.00 |
| Natural Calcium Carbonate | 30.00 | 42.00 | 0.00 | 0.00 | 30.00 | 20.00 |
| Thickener Silica | 3.00 | 2.00 | 0.00 | 0.00 | 4.00 | 8.00 |
| Magnesium Alum. Silicate | 1.00 | 1.00 | 3.50 | 0.00 | 0.00 | 0.00 |
| NaCMC Type 7/500T | 0.00 | 0.00 | 1.20 | 1.00 | 0.00 | 0.00 |
| NaCMC Type 8 | 1.60 | 1.00 | 0.00 | 0.00 | 1.60 | 1.30 |
| Xanthan gum | 0.00 | 0.00 | 0.20 | 0.00 | 0.00 | 0.00 |
| Sorbitol, N.C. (70 wt. % aq soln) | 21.00 | 15.00-25.00 | 0.00 | 0.00 | 21.00 | 13.00 |
| Glycerin, vegetable - USP | 0.00 | 0.00 | 9.00 | 12.00-18.00 | 0.00 | 0.00 |
| Tetrasod. Pyrophosphate | 0.00 | 0.00 | 0.50 | 0.25-0.75 | 0.00 | 0.00 |
| Sod. Bicarbonate | 0.10 | 0.05-1.00 | 0.50 | 0.25-0.75 | 0.10 | 0.00 |
| Sod. Carbonate (Soda Ash) | 0.40 | 0.20-0.60 | 0.00 | 0.00 | 0.40 | 0.90 |
| Sod. Hydroxide (50 wt. % aq Sol'n) | 0.00 | 0.00 | 0.08 | 0.05-0.50 | 0.00 | 0.00 |
| NaMFP - USP | 1.10 | 1.00-1.50 | 1.10 | 1.00-1.50 | 1.10 | 1.10 |
| Sodium Lauryl Sulfate | 1.90 | 1.00-2.00 | 1.76 | 1.00-2.00 | 1.90 | 1.90 |
| Sodium Saccharin | 0.15 | 0.10-1.00 | 0.25 | 0.10-1.00 | 0.15 | 0.15 |
| Flavor | 0.80 | 1.00 | 0.85 | 0.95 | 0.80 | 0.80 |
| Benzyl Alcohol | 0.30 | 0.10-1.00 | 0.30 | 0.10-1.00 | 0.30 | 0.30 |
| Demineralized Water | 38.65 | 25.00-35.00 | 53.76 | 30.00-40.00 | 38.65 | 52.55 |
| Viscosity (×10,000 cps)/YS (Pa) @ RT, V74 spindle | | | | | | |
| Initial | 59/319 | 51/290 | 23/86 | 22/118 | 39/57 | 20/50 |
| 1 day | 58/319 | 53/290 | 28/94 | 32/257 | 40/57 | 20/52 |
| 3 days | 62/319 | 56/319 | 30/129 | 40/290 | 42/76 | 23/107 |
| 1 Week | 64/319 | 50/319 | 36/235 | 45/290 | 43/76 | 32/95 |
| 1 Month | 64/290 | 55/319 | 38/235 | 48/290 | 45/113 | 44/129 |
| Recovery Time (seconds) | | | | | | |
| T80 | 10 | 12 | 15 | 25 | 21 | 43 |
| T90 | 18 | 22 | 20 | 49 | 44 | 82 |

The recovery time was determined using a TA Instruments ARES 2 rheometer with concentric cylinders geometry. A shear rate of $100 \text{ sec}^{-1}$ was applied to the formulation under test for 60 seconds, then the shear rate was stepped down to $1 \text{ sec}^{-1}$ at the point of time which is taken here as t=0. Shear stress first rapidly drops, then passes through a minimum (called "undershoot") and then increases as the structure of the toothpaste recovers. The shear stress eventually saturates, i.e. reaches a steady value (in some cases it may slightly oscillate around its steady value). This steady value (or the maximum of this slightly oscillating shear stress) is Example 11

Sensory panel experiments were also carried out to determine whether or not the compositions of the present invention (with lower calcium carbonate concentrations than the benchmark formulations) would provide significantly different texture, flavor release and overall mouthfeel profiles compared to the benchmark products. However, the sensory panels described below indicated no significant differences among the compositions of the present invention in comparison to benchmark formulas. It was also possible to decrease the flavor level in these high water formulations and still achieve parity ratings in key sensory attributes.

Four trained expert sensory panels were fielded comparing sensorial attributes of compositions of the present invention to benchmark formulas of different compositions and flavor systems. The initial study compared a prototype of 3.85 weight % MAS/20 weight % PCC of equal flavor level (Formula N) to the benchmark formulation as described in Table 1, and it was found that Formula N provided greater flavor intensity during brushing and at several time points after expectorating. A subsequent study indicated parity sensory ratings for the same formula N, but with 10% reduced flavor loading compared to the benchmark formula of Table 1. These first two studies utilized the same flavor composition of predominantly anethole character.

A third expert panel study evaluated a similar prototype (Formula T) with 3.5 weight % MAS/27 weight % PCC, which prototype had 10% reduced flavor (as compared to the benchmark Y). The flavor was primarily of spearmint character. Again, it was found that the MAS/PCC toothpaste of lower flavor loading provided no significant differences in sensory attributes compared to the 41 weight % PCC benchmark formulation.

A final expert panel study compared benchmark formula S (having 42 weight % NCC abrasive) with a composition containing 1 weight % MAS/30 weight % NCC (formula R), which had 20% reduced flavor loading as compared to the benchmark formula. Results showed that formula R (with similar calcium carbonate loading but greatly reduced flavor level) had no significant downsides on key sensory attributes compared to benchmark S. Interestingly, a 30% NCC non-MAS formula (Formula Z) was also fielded in this study. This formula differs from Formula R only in that 1 weight % MAS was replaced by 1 weight % thickener silica. Unlike the MAS option (Formula R), it showed significantly reduced flavor intensity at several brushing and after expectorating timepoints compared the benchmark (Formula S).

We claim:

1. An oral care composition comprising, by total weight of the composition:
   (a) 15 to 35 weight % calcium carbonate;
   (b) 0.5 to 2 weight % cellulose ether thickening agent;
   (c) 1 to 6 weight % clay thickening agent; and
   (d) at least 40 weight % water;
   wherein, when the composition comprises less than 28 weight % calcium carbonate and less than 4 weight % clay thickening agent, the cellulose ether thickening agent is present in an amount of greater than 1 weight;
   wherein said cellulose ether thickening agent is sodium carboxymethylcellulose; and
   wherein said clay thickening agent is magnesium aluminum silicate.

2. The oral care composition of claim 1, comprising from 18 to 28 weight % calcium carbonate, based on the total weight of the composition.

3. The oral care composition of claim 1, wherein the calcium carbonate comprises natural calcium carbonate.

4. The oral care composition of claim 1, wherein the calcium carbonate comprises precipitated calcium carbonate.

5. The oral care composition of claim 1, comprising from 2.5 to 4 weight % clay thickening agent, based on the total weight of the composition.

6. The oral care composition of claim 1, comprising from 1 to 1.5 weight % cellulose ether thickening agent, based on the total weight of the composition.

7. The oral care composition of claim 6, further comprising microcrystalline cellulose present in an amount of from 0.4 to 0.9 weight %, based on the total weight of the composition.

8. The oral care composition of claim 7, wherein the ratio of microcrystalline cellulose to cellulose ether thickening agent is from 1:1 to 1:3.5 by weight.

9. The oral care composition of claim 6, comprising 20 to 27 weight % calcium carbonate and 2.5 to 4 weight % magnesium aluminum silicate, based on the total weight of the composition.

10. The oral care composition of claim 1, further comprising an additional structuring agent selected from xanthan gum, carrageenan, alginate, a thickening silica and guar gum.

11. The oral care composition of claim 10, wherein the additional structuring agent is a thickening silica and the ratio of thickening silica to clay thickening agent is from 4:1 to 2:1 by weight.

12. The oral care composition of claim 1, comprising the calcium carbonate in an amount of from 20 to 30 weight % and the cellulose ether thickening agent in an amount of from 1 to 2 weight %, based on the total weight of the composition.

13. The oral care composition of claim 1, further comprising a humectant selected from sorbitol, glycerin, xylitol, polyethylene glycol, propylene glycol, and combinations thereof.

14. The oral care composition of claim 13, wherein the ratio of humectant to cellulose ether thickening agent is from 5:1 to 10:1 by weight.

15. The oral care composition of claim 1, wherein the composition has a pH of from 9.2 to 10.2.

16. The oral care composition of claim 15, wherein the composition further comprises a buffer system, the buffer system being:
   (a) a combination of sodium silicate and tetrasodium pyrophosphate;
   (b) a combination of sodium hydroxide, sodium bicarbonate and tetrasodium pyrophosphate; or
   (c) a combination of sodium bicarbonate and sodium carbonate.

17. The oral care composition of claim 1, wherein the composition is a toothpaste, a tooth gel, or a combination thereof.

18. The oral care composition of claim 1, wherein the viscosity of the composition is from 100,000 to 1,000,000 cps as measured at 25° C. at 1 rpm using a Brookfield Viscometer Model HADV-II+Pro and a V74 spindle.

* * * * *